May 7, 1940. T. J. MORRIS Plant Pat. 394
ROSE PLANT
Filed Sept. 2, 1939
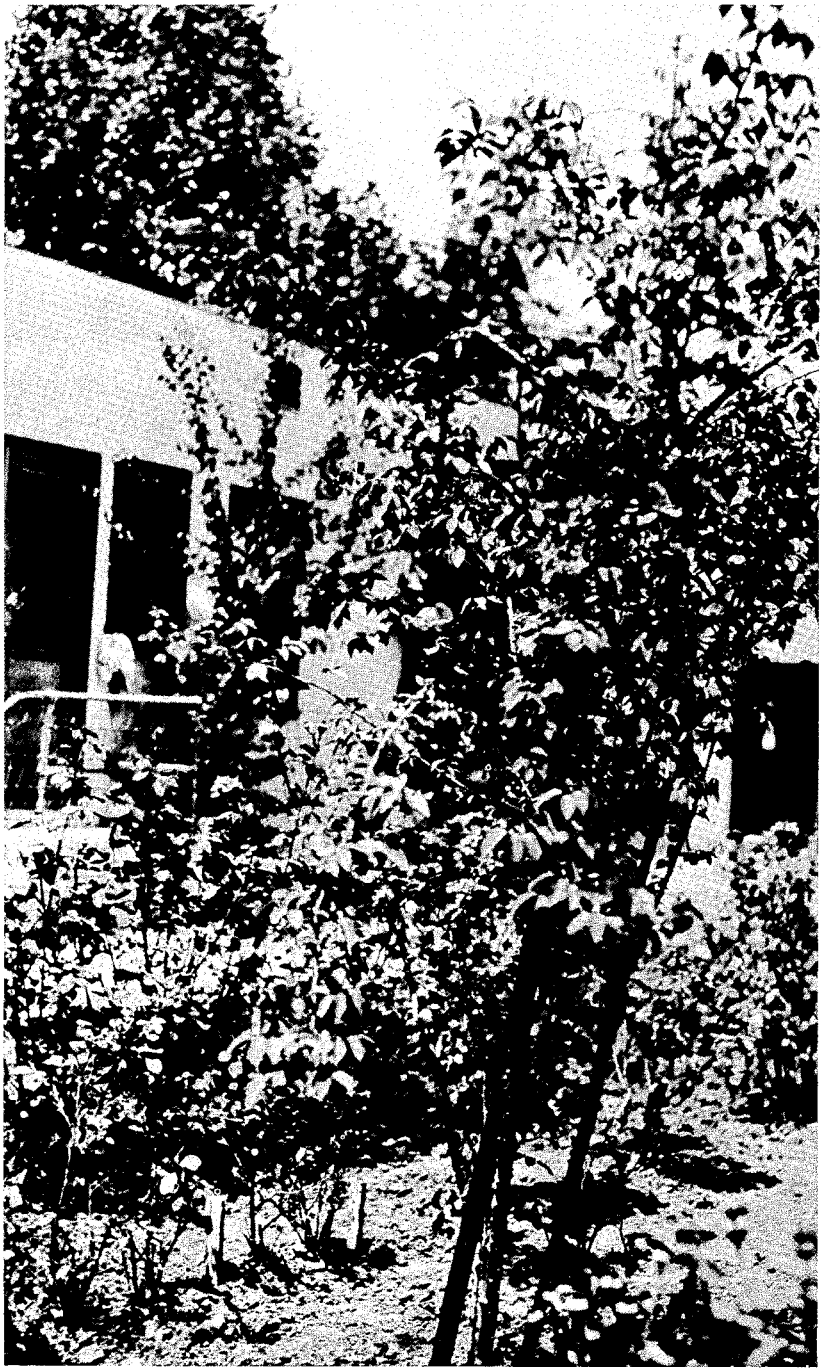
INVENTOR
T. J. Morris
By Robbins & Robbins
ATTORNEYS Patented May 7, 1940 Plant Pat. 394

UNITED STATES PATENT OFFICE

394

ROSE PLANT

Theodore J. Morris, Van Nuys, Calif., assignor to Western Rose Co., San Fernando, Calif., a copartnership composed of Albert B. Morris and Theodore J. Morris Application September 2, 1939, Serial No. 293,158

1 Claim. (Cl. 47—61)

The present discovery is a new and distinct variety of hybrid tea rose plant originating as a sport of the well known variety of Mrs. Sam McGredy.

This new rose was discovered by me on a plant grown in the gardens of the Western Rose Co., in San Fernando, California, and is distinguished from its parent only in that it is a very strong climber. In all other respects it is identical with its parent, including the shape and color of its flower.

The new rose has been asexually reproduced and it has been found that its distinguishing characteristic holds through succeeding propagations.

Since the parent variety is known commercially, no colored illustration is necessary, and the drawing simply illustrates in black and white the original plant of the new variety and clearly discloses the climbing habit of the plant by association with surrounding objects.

The following detail description is given for purposes of convenience. The color terminology used is in accordance with the standard rose record of the American Rose Society for the variety "Mrs. Sam McGredy."

Parentage: Sport.
*Parent.*—Mrs. Sam McGredy.
Classification:
*Botanic and commercial.*—Hybrid tea.

*Flower*

(Observations made at ten o'clock in the morning at Van Nuys, California.)

Blooming habit:
*Recurrent.*—Continuous.
*Other habit*—Very strong climber.
Bud:
*Size.*—Very large.
*Form*—Very long. Is not affected by wet weather but fades during hot weather.
*Color.*—When sepals first divide—Copper Orange.
When petals begin to unfurl—Copper Orange with Lincoln Red. When half blown: inside of petals—Copper Orange; reverse of petals—Light Copper Orange.
*Sepals.*—Smooth edge.
*Calyx.*—Shape—pear. Size—large. Aspect—smooth.
*Peduncle.*—Length—medium. Aspect—smooth. Color—Medium Green. Strength—bending.
*Opening.*—Bud opens well. Is not affected by adverse conditions.
Bloom:
*Size.*—Large.
*Average size when fully expanded.*—Four inches.
*Borne.*—Singly.
*Stems.*—Medium length, normal strength.
*Form.*—When first open—cupped. Permanence—outer petals curl back.
*Petalage.*—Double. Number of petals under normal conditions—32.
*Color.*—Center of flower—Deep Copper. Outer petals—Copper flushed with Orange. Base of petals (aiglet)—flushed with Lincoln Red. Inside of petals—Copper Orange. Reverse of petals—Copper Orange flushed with Lincoln Red. General tonality for a distance—Copper.
Petals:
*Texture.*—Thick. Is not affected by wet or hot weather.
*Appearance.*—Inside—shiny, outside—shiny.
*Form.*—Oval.
*Arrangement.*—Imbricated.
*Persistence.*—Drop off cleanly.
*Fragrance.*—Slight. Nature—centrifolia.
*Lasting quality.*—As cut flower, fair.
Genital organs:
*Stamens, anthers.*—Medium size. Color—Yellow. Arrangement—regular around styles.
*Stamens, filaments (threads).*—Long. Color—Yellow.
*Pollen.*—Lemon Yellow.
*Styles.*—Thin.
*Stigmas.*—Yellow.
*Ovaries.*—All enclosed in calyx.
Fruit: Variety is fertile with its own pollen.
*Form.*—Flat headed, pear shaped.
*Aspect.*—Smooth.
*Color at maturity.*—Orange.
*Sepals.*—Permanent, curled.

*Plant*

Form: Climber.
Growth: Very vigorous.
Foliage: 5 to 7 leaflets.
*Size.*—Large
*Quantity.*—Abundant.
*Color.*—New foliage: upper side—Bronzy; old foliage: upper side—Normal Green.
*Shape.*—Oval.
*Texture.*—Upper side—glossy. Under side—smooth. Ribs and veinings—Light.

*Edge.*—Serrated.
*Serration.*—Single.
*Rachis.*—Color—Green. Under side—prickles.
*Stipules.*—Medium length, serrated.
*Disease resistance.*—Susceptible to mildew.

Wood:
*New wood.*—Color—Bronzy. Bark—smooth.
*Old wood.*—Color—Bronze. Bark—smooth.

Thorns (thorns are divided into thorns, prickles, and short needles):
*Thorns.*—Quantity on main stalks from base and on laterals from stalk—ordinary. Form—Narrow base, hooked downward. Color when young—Red. Position—irregular.
*Prickles.*—Quantity on main stalks—few. Color—Brown.
*Short needles.*—Quantity on main stalks—none, on laterals—few.

I claim:

A new and distinct variety of hybrid tea rose plant characterized as to novelty by its climbing habit, substantially as set forth.

THEODORE J. MORRIS.